United States Patent [19]

Cobb

[11] Patent Number: 4,763,525

[45] Date of Patent: Aug. 16, 1988

[54] APPARATUS AND METHOD FOR DETERMINING THE QUANTITY OF GAS BUBBLES IN A LIQUID

[75] Inventor: Wesley N. Cobb, University Heights, Ohio

[73] Assignee: The Standard Oil Company, Cleveland, Ohio

[21] Appl. No.: 852,608

[22] Filed: Apr. 16, 1986

[51] Int. Cl.⁴ ............................................. G01N 29/00
[52] U.S. Cl. ..................................... 73/599; 73/61 R; 73/627
[58] Field of Search ............... 73/600, 599, 61 R, 627, 73/584 U.S. only

[56] References Cited

U.S. PATENT DOCUMENTS

| | | | |
|---|---|---|---|
| 3,240,674 | 3/1966 | Ledwidge | 176/19 |
| 3,381,525 | 5/1968 | Kartluke et al. | 73/67 |
| 3,622,958 | 11/1971 | Tucker et al. | 340/1 R |
| 4,527,420 | 7/1985 | Foote | 73/61 R |

FOREIGN PATENT DOCUMENTS 3210591 10/1983 Fed. Rep. of Germany ........ 73/627

OTHER PUBLICATIONS

"An Ultrasonic Void Fraction Detector Using Compressional Stress Waves in a Wire Helix" by A. E. Arave; Pub. Oct. 1970.

Primary Examiner—Stewart J. Levy
Assistant Examiner—Louis M. Arana
Attorney, Agent, or Firm—Jeffrey A. Wyand; Joseph G. Curatolo; Larry Evans

[57] ABSTRACT

A method and apparatus for measuring the quantity of bubbles in a gas/liquid mixture. An ultrasonic wave is launched into the mixture and the magnitudes of two reflected waves are measured and compared. The logarithm of the magnitudes of the reflected waves is a measure of the quantity of gas content. The method and apparatus are suitable for measuring gas bubble content repetitively in a mixture turbulently flowing through a conduit.

23 Claims, 7 Drawing Sheets

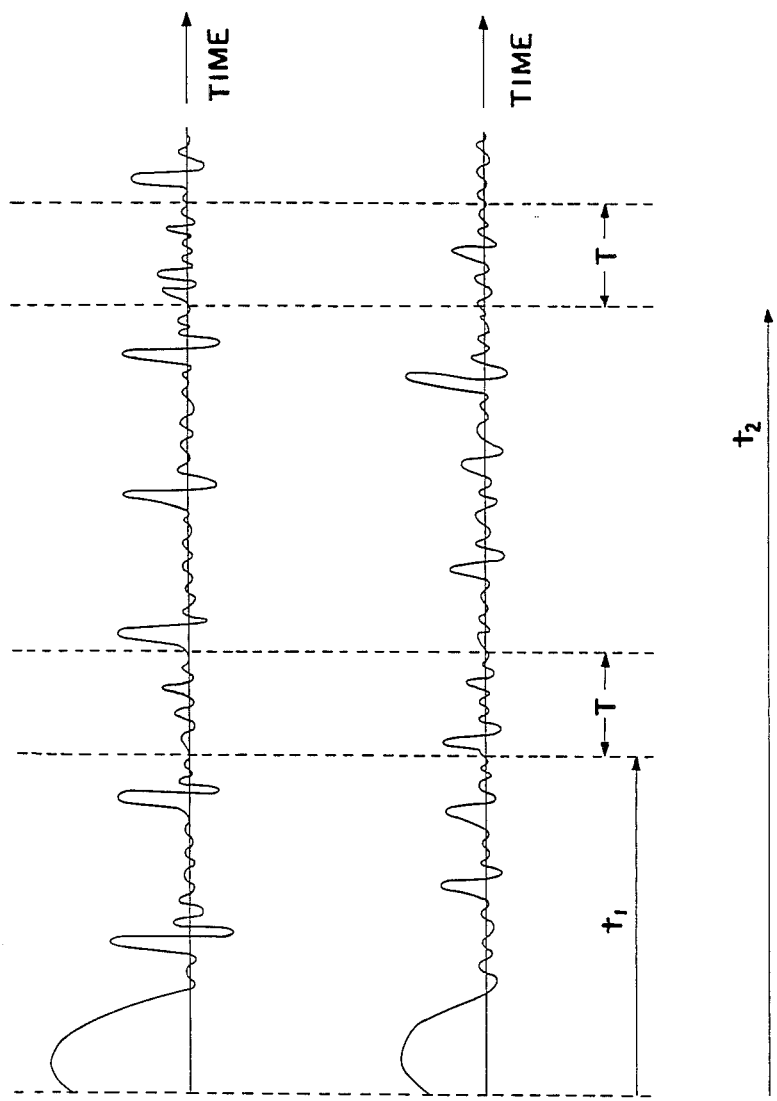

APPARATUS AND METHOD FOR DETERMINING THE QUANTITY OF GAS BUBBLES IN A LIQUID

BACKGROUND

This invention concerns apparatus and methods for measuring the quantity of bubbles present in a liquid containing gas bubbles. The method and apparatus are particularly useful in determining the gas bubble content of liquids turbulently flowing through pipes. The determination is made at a fixed location in the pipe so that the gas bubble content of the flowing liquid can be continuously monitored.

Techniques for determining the presence or absence of gas bubbles in liquids are known. Apparatus for determining the onset of the formation of bubbles, i.e. cavitation or boiling, but not the proportion of bubbles, has been described by a number of patentees. In U.S. Pat. No. 3,381,525 to Kartluke et al., sound waves are launched into a liquid. The liquid is monitored for sound waves at subharmonic frequencies of the launched sound waves. When subharmonic waves are detected, cavitation is imminent or has begun. In U.S. Pat. No. 3,240,674 to Ledwidge, a similar technique is used. No sound waves are added to the liquid. Instead, the frequencies of sound waves in the liquid are monitored for a selected spectrum peak that indicates localized boiling, a prelude to boiling of the entire liquid volume. U.S. Pat. No. 3,622,958 to Tucker et al. discloses a number of methods of detecting the existence of gas bubbles in a liquid. Waves at a fundamental frequency are launched into a liquid by a first transducer and waves at harmonic frequencies are detected by a second transducer. Detection of harmonic frequency signals indicates the presence of gas bubbles. Alternatively, reflected waves at harmonic frequencies are detected by the same transducer that launches the fundamental frequency wave. In still another embodiment, multiple frequency sound waves are launched into the liquid which is monitored for waves having frequencies equal to a sum or difference of two of the frequencies of the launched waves.

A complex method of determining the fraction of steam in a steam/water mixture was disclosed by Arave in "An Ultrasonic Void Fraction Detector Using Compressional Stress Waves in A Wire Helix" published October 1970 by the Idaho Nuclear Corporation for the U.S. Atomic Energy Commission. In this method, a stress wave is propagated on the surface of a wire helix that is immersed in a liquid-gas mixture. The attenuation of the stress wave from one end of the helix to the other is measured to determine the "void fraction", i.e. bubble content, of the liquid in the local volume adjacent the surface of the helix.

The known technology does not provide a simple, reliable method of quantitatively measuring the bubble content of a liquid-gas mixture. The invention provides a simple method and apparatus for measuring the bubble content in a liquid and especially in a turbulently flowing liquid.

SUMMARY OF THE INVENTION

In the invention, longitudinal waves, such as ultrasonic waves, are launched during a first time period into a liquid containing gas bubbles. Those waves are attenuated as they propagate through the mixture and are reflected by the bubbles in the mixture. Reflected longitudinal waves are detected during distinct second and third time periods and the relative magnitudes of the reflected waves are determined and compared. The ratio of the magnitudes of the waves reflected during each of the time periods is directly related to the gas content of the liquid. The logarithm of the ratio of the magnitudes of the reflected waves is directly proportional to the gas content, i.e. bubble volume, of the mixture.

Preferably, the same ultrasonic transducer is used to launch the waves and to detect the reflected waves, although separate sending and receiving transducers can be employed. An electrical pulse is applied to the transducer during a first time period to launch longitudinal waves. Then, during each of the subsequent second and third time periods, the transducer receives reflected longitudinal waves, converting them to electrical magnitude signals. Preferably, separate signal processing channels are provided for receiving each of the second and third time period electrical magnitude signals, sensing the value of each magnitude signal received during the respective second and third time periods and simultaneously delivering these values to logarithmic amplifiers. The logarithmic amplifiers generate signals proportional to the logarithm of the amplitude of the applied signals. The difference of these logarithmic signals, i.e. the logarithm of the ratio of the intensities of the reflected waves, is obtained as the output signal of a differential amplifier. The magnitude of that output signal is directly proportional to the gas content of the liquid. The output signal is preferably filtered to remove rapid time variations and produce a smooth signal. For a continuous measurement of gas content, it is preferred that the first, second and third time periods follow each other sequentially and repetitively, with an output signal being supplied by the differential amplifier at the conclusion of each third time period.

The transducers used may be in direct contact with the liquid containing the gas bubbles or may be remote from the liquid. In the latter situation, the transducer or transducers can be affixed to the outside wall of the vessel containing the liquid. In that event, the timing of the second and third time periods with respect to the first time period is selected so that wave reflections from the walls of the vessel are not detected.

The invention provides an effective, reliable, inexpensive and simple method and means of accurately measuring the gas bubble content of a liquid. The use of through-transmission wave attenuation measurements, which is ineffective when large vessels are used, is avoided. The invention permits a non-intrusive measurement so that the transducers and liquid do not contact, contaminate or foul each other.

The invention may be more fully understood by reference to the detailed description taken in conjunction with the following drawing figures.

BRIEF DESCRIPTION OF DRAWINGS

FIG. 2a is a plot over time of the amplitude of reflected longitudinal waves detected by an embodiment of the invention; FIG. 2b is a plot over time of the amplitude of reflected longitudinal waves detected in another embodiment of the invention.

DETAILED DESCRIPTION OF PREFERRED EMBODIMENTS

The invention uses the known attenuation characteristic of longitudinal waves in a lossly medium such as a liquid. The presence of gas bubbles in a liquid alters and increases the attenuation of a plane longitudinal wave propagating through the gas/liquid mixture.

The magnitude of a plane longitudinal, i.e. pressure or ultrasonic, wave propagating through an attenuating medium is known to be $$P_x = P_o e^{-\alpha(f,\epsilon)x} \tag{1}$$

where $P_x$ = the magnitude of the wave at point x measured from a reference point;

$P_o$ = the magnitude of the wave at a reference point, x=0;

x = the distance from the reference point to point x; and $\alpha(f,\epsilon)$ = the attenuation coefficient which is a function of the frequency, f, of the wave and the gas percentage, $\epsilon$, in the medium.

Longitudinal waves propagate in liquids at different velocities depending upon the characteristics of the liquid, such as viscosity, and density, and on the characteristics of the wave, such as frequency. The presence of bubbles in a liquid causes scattering of waves, effectively increasing the attenuation. The precise propagation parameters of a particular liquid or gas/liquid mixture are not quantitatively predictable. Therefore the propagation parameters of a particular mixture are determined by measurement.

Figure 1B:
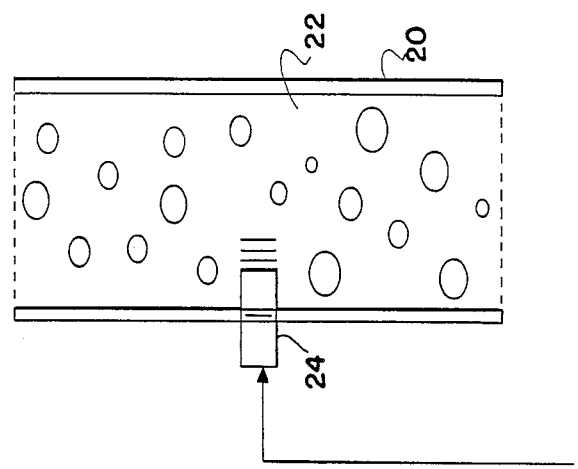
FIG 1b is a partial cross sectional view of another embodiment of the invention.
Figure 1A:
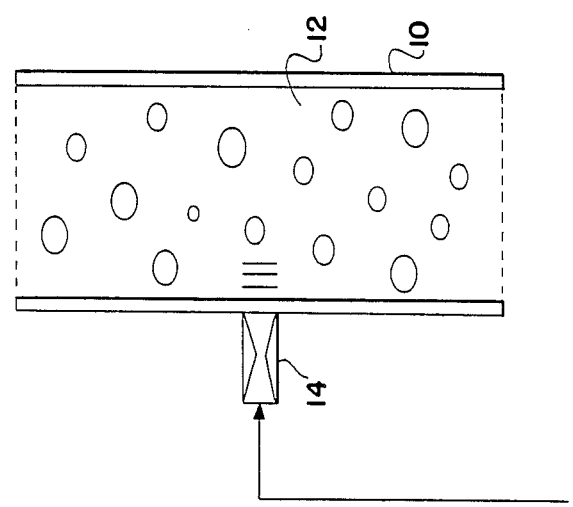
FIG. 1a is a schematic, partial cross section view of an embodiment of the invention.

In FIGS. 1a and 1b, two embodiments for launching and detecting longitudinal waves according to the invention are shown. In FIG. 1a, the walls of a vessel 10 confine a gas bubble/liquid mixture 12. As indicated by the open ends of the vessel, vessel 10 may be a pipe or conduit through which the mixture is flowing. An ultrasonic transducer 14 is affixed to the outside of a wall of vessel 10 and therefore does not directly contact mixture 12. The ultrasonic transducer converts electrical signals to pressure waves and vice versa. That is, an electrical pulse applied to the transducer causes it to respond mechanically and launch a longitudinal wave in the medium which it contacts. In addition, a longitudinal wave striking the transducer causes it to deform mechanically and generate an electrical pulse. Such transducers are conventional and piezoelectric transducers suitable for use in the invention are commercially available from Panametrics, Inc. of Waltham, Mass.

An alternative transducer configuration is shown in FIG. 1b. There, a transducer 24 projects through a wall of a vessel 20 and is in direct contact with a liquid/gas mixture 22. This arrangement has the disadvantage of direct contact between the transducer and mixture 22 which could result in the fouling of the liquid or transducer. However, in the embodiment of FIG. 1a, longitudinal waves are launched in the walls of vessel 10 and reflected from the surfaces of those vessels. There are no wall reflected waves in the embodiment of FIG. 1b since there is direct contact between transducer 24 and liquid 22.

When a longitudinal wave is launched into liquid/gas mixture 12 or 22, the wave is reflected by the bubbles in the liquid. The reflected wave gradually decreases in magnitude as a result of its travel from the transducer to the point of reflection and back to the transducer. If the reflected wave amplitude, that is, the transducer signal, is measured at two different times, the reference pressure of Equation 1 may be eliminated. Specifically if signals $V_1$ and $V_2$ are detected at times $t_1$ and $t_2$, then $$(V_2/V_1) = e^{-\alpha(f,\epsilon)\Delta x}$$

where $\Delta x$ represents the propagation distance covered between $t_1$ and $t_2$. That is, $\Delta x$ equals the speed of sound in the mixture multiplied by the delay between $t_1$ and $t_2$. Then $$(f,\alpha) = \alpha 8 \, 1/\Delta x \, \ln(V_1/V_2) \tag{2}$$

For a particular liquid with varying bubble content and a particular frequency wave, the attenuation coefficient will vary only with gas percentage, i.e. bubble content, $\epsilon$. This relationship can be used to determine, quantitatively, the bubble content of the liquid/gas mixture.

Examples of reflected waveforms detected over time by the apparatus of FIGS. 1a and 1b are shown in FIGS. 2a and 2b, respectively. In FIGS. 2a and 2b, the amplitude of the waveforms is plotted as a function of time. In FIGS. 2a, echos from the surfaces of vessel 10 appear prominently and are much larger in amplitude than the echos from the gas bubbles. These vessel wall reflections are absent from FIG. 2b.

After a first time period during which a longitudinal wave is launched, there is a listening period. FIGS. 2a and 2b show two listening time "windows" of equal duration. After time $t_1$, the first window, i.e. the second time period, "opens" for a period T. After time $t_2$ elapses, measured from the launching of waves into the liquid/gas mixture, the second window, i.e. the third time period, "opens" for the same period T. During these second and third time periods, $V_1$ and $V_2$ are measured, respectively, for the calculation of $\alpha$ in Equation 2. As indicated in FIG. 2a, it is important to select times $t_1$ and $t_2$ to avoid detecting the reflections from the vessel walls since those reflections do not involve the bubble content of the mixture. The voltage signal, i.e. the amplitude of the reflected wave, detected during each window varies during time T. With respect to Equation 2, it is the peak voltage or pressure signal that is measured during each "listening" time period that constitutes $V_1$ or $V_2$.

Figure 3:
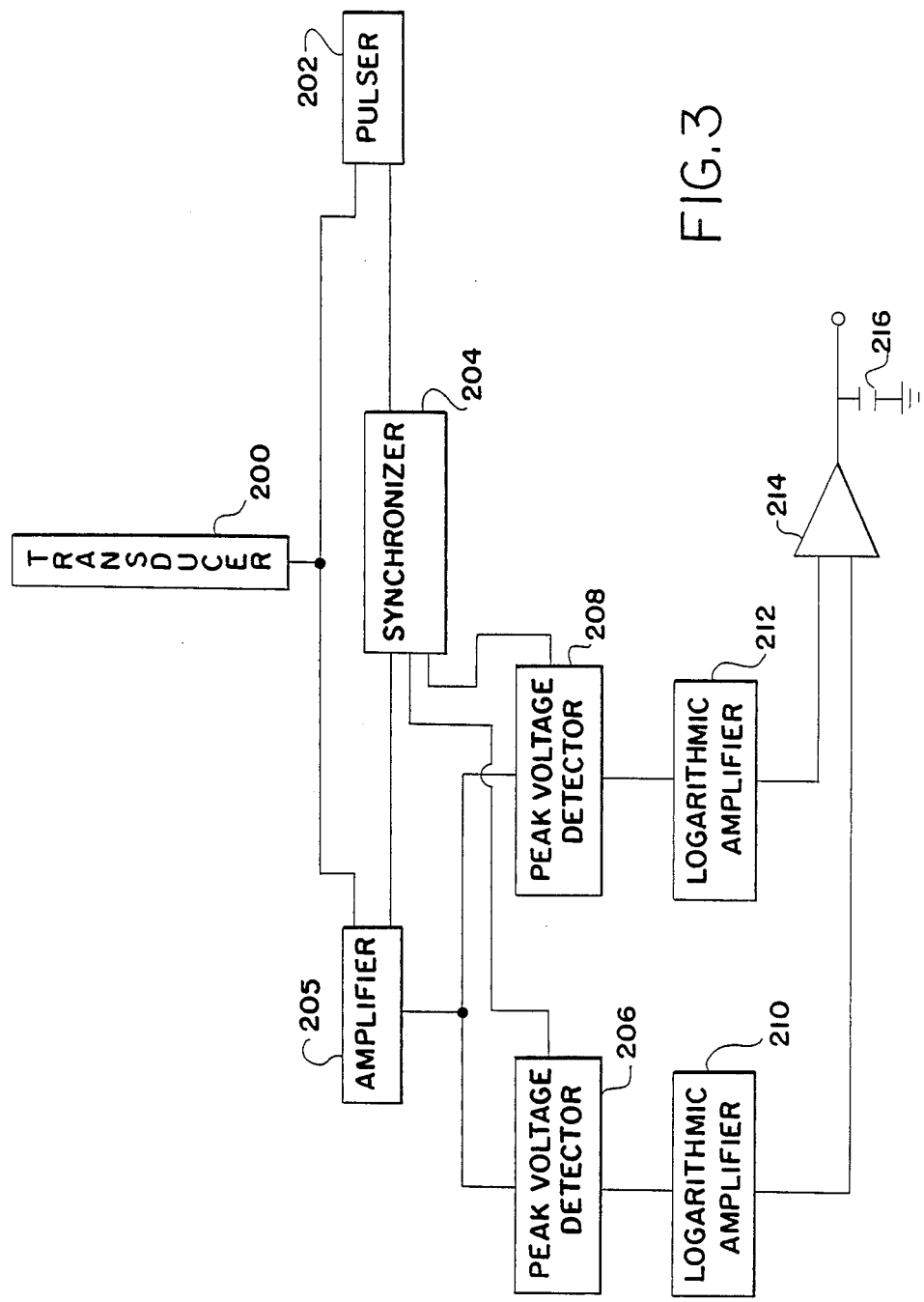
FIG. 3 is a schematic block diagram of an embodiment of the invention.

Apparatus for processing the electrical signals produced in response to the reflected waves detected by a transducer 200, like transducers 14 and 24, is shown schematically in FIG. 3. Transducer 200 is connected to a pulser 202 that supplies a voltage pulse during a first time period to launch longitudinal waves. In response to the voltage pulse, transducer 200 launches a longitudinal wave consisting of a few pressure cycles at the selected frequency. Pulser 202 is controlled by a synchronizing means 204, such as a timer that emits enabling pulses on a predetermined schedule. Pulser 202 is triggered during a first time period by synchronizer 204. After the first time period, pulser 202 is silent, under the influence of synchronizer 204, until after the passage of the second and third time periods. Synchronizer 204 may also control an amplifier 205 that receives the electrical signals generated by transducer 200 in response to echo signals. Synchronizer 204 may deactivate amplifier 205 during the first time period so it does not receive and is not overloaded by the launching pulse sent to transducer 200 by pulser 202. The amplified output signal from amplifier 205 is applied to the input terminals of gated peak voltage detectors 206 and 208. At the expiration of time $t_1$ (see FIG. 2), synchronizer 204 enables gated peak voltage detector 206 for a second time period. During that time period, peak detector 206 receives a first electrical signal generated by transducer 200, senses the peak amplitude, $V_1$, of the signal during the second time period and holds it as a first magnitude signal. Likewise, during a third time period, after time $t_2$, synchronizer 204 enables gated peak voltage detector 208 to receive a second electrical signal from transducer 200. Normally the first, second and third time periods are separated from each other in time. In any case, the time periods do not overlap. Detector 208 senses the peak amplitude, $V_2$, of the second electrical signal during the third time period and holds it as the second magnitude signal. The held first and second magnitude signals are applied, under the control of synchronizer 204, to logarithmic amplifiers 210 and 212, respectively. The logarithmic amplifiers convert the first and second magnitude signals to first and second logarithmic signals having magnitudes that are proportional to the logarithms of the amplitude of the magnitude signals. The first and second logarithmic signals are applied to the positive and negative input terminals of a differential amplifier 214. Amplifier 214 produces a signal proportional to the difference between the amplitudes of the input signals. That is, the output signal of amplifier 214 is proportional to the natural logarithm of $(V_1/V_2)$ which, from Equation (2), is proportional to the wave attenuation coefficient, $\alpha$.

That attenuation coefficient is an indicator of the bubble content of the liquid/gas mixture. The output signal can vary rapidly with time. To smooth the output signal, it is desirable to add an electrical filter, such as a low pass filter, to differential amplifier 214. A capacitor 216 connected from the output terminal of amplifier 214 to ground is a simple embodiment of such a filter.

The smoothed output signal may be applied to any sort of indicating device to display the bubble percentage in the liquid/gas mixture. For example, an analog or digital voltmeter, a strip chart recorder or a computer input might receive the signal for direct or remote monitoring either during real time or at some later time, of bubble content.

It is necessary to calibrate the output signal to determine the percentage of gas bubbles present in a mixture. It has been determined experimentally that the gas percent in a turbulent multiphase mixture is given by $$\epsilon = A\alpha + B = A/\Delta < \ln(v_1/V_2) > + B \quad (3)$$

A, B and $\Delta x$ are all constants for a mixture of a particular gas and liquid, for a particular wave frequency, for a fixed apparatus geometry and for constant listening window positions in time. The values of these constants need not be determined since each embodiment of apparatus according to the invention is individually calibrated for a particular gas/liquid mixture. The calibration takes into account the value of all the constants.

Figure 4:
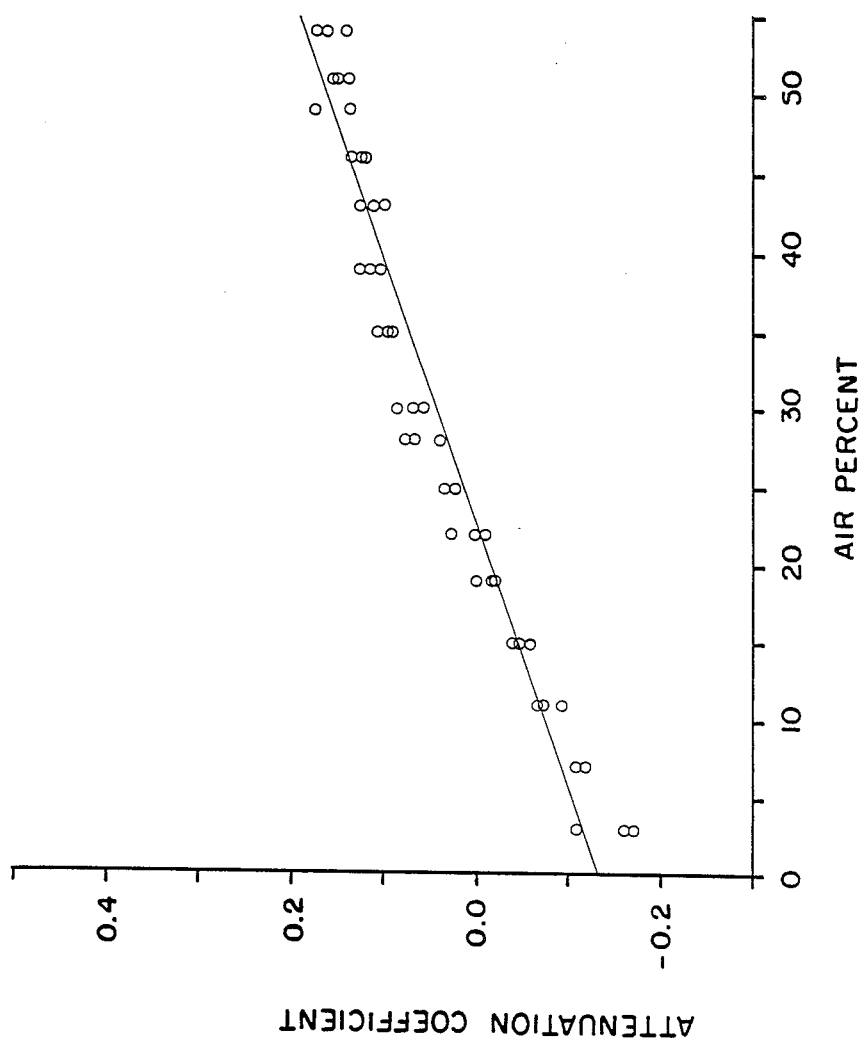
FIGS. 4-7 are graphs of measured results of the quantities of gas bubbles in a gas bubble-liquid mixture according to the invention.
Figure 5:
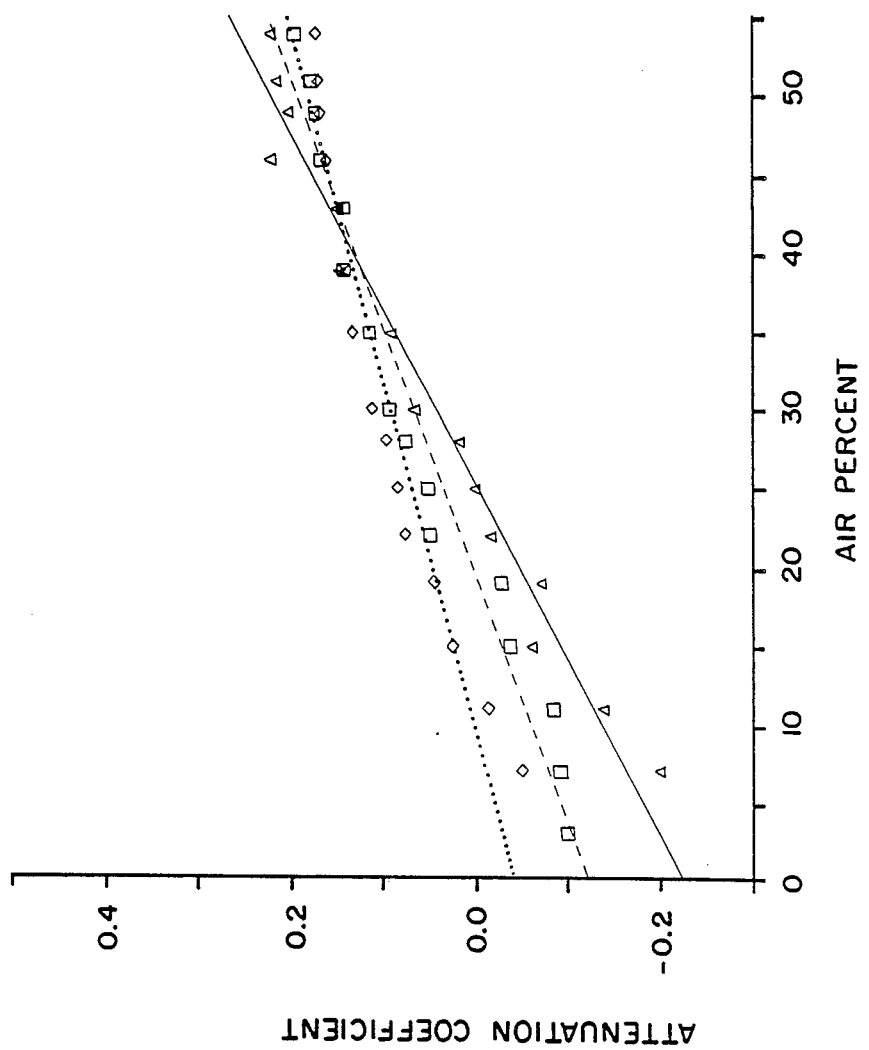

FIGS. 4-7 illustrate the measured linearity of the relationship between the attenuation coefficient and gas bubble content for different mixtures and apparatus. FIGS. 4 and 5 display measured results for an embodiment of apparatus in which the transducer is in direct contact with the liquid/gas mixture. In FIG. 4, the transducer was exposed to a water/air mixture and excited with an abrupt voltage change, i.e. a pulse. In response to the excitation, a wave at the 2 MHz natural ringing frequency of the transducer was launched into the mixture. The transducer was pulsed at a 1 kHz rate. One thousand readings of the reflected electrical signal pairs $V_1$ and $V_2$ were recorded for each water/air mixture. The air bubble amount ranged from 5 percent to 55 percent, approximately in 5 percent increments. The time windows each had a width of 1.6 microseconds, the first and second time window beginning 16 and 32 microseconds after the wave launching pulse. The linearity of the relationship is clear. In FIG. 5, the effect of changing the separation in time of the time windows, i.e. the second and third periods, is shown. The test conditions were the same as those for FIG. 4 except the time windows were set at 8 and 16 microseconds for the plotted triangles, 8 and 32 microseconds for the plotted squares and 8 and 48 microseconds for the plotted diamonds. Again the strong linear relationship is evident. The slope is dependent on the window spacing, but not to a large extent. Of course, since the delay time is longer when the second time window is delayed, $\Delta x$ of Equation (2) is different for each of the plotted lines.

Figure 6:
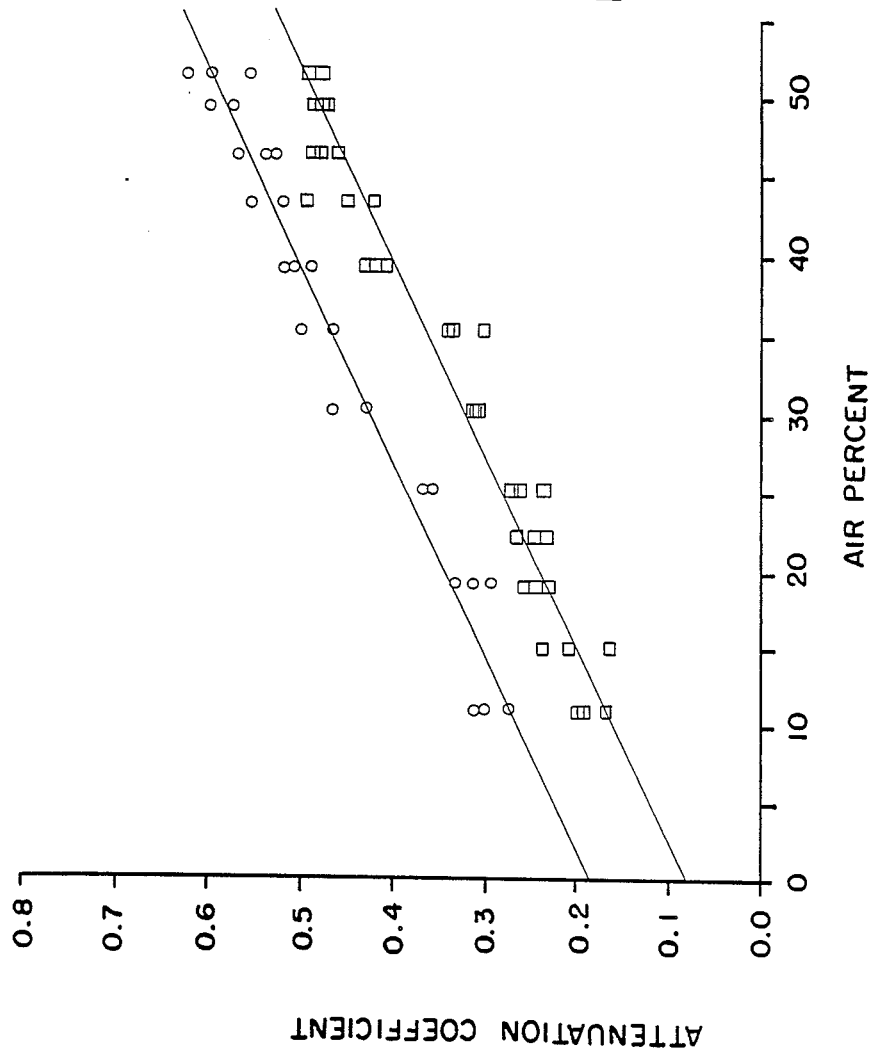
Figure 7:
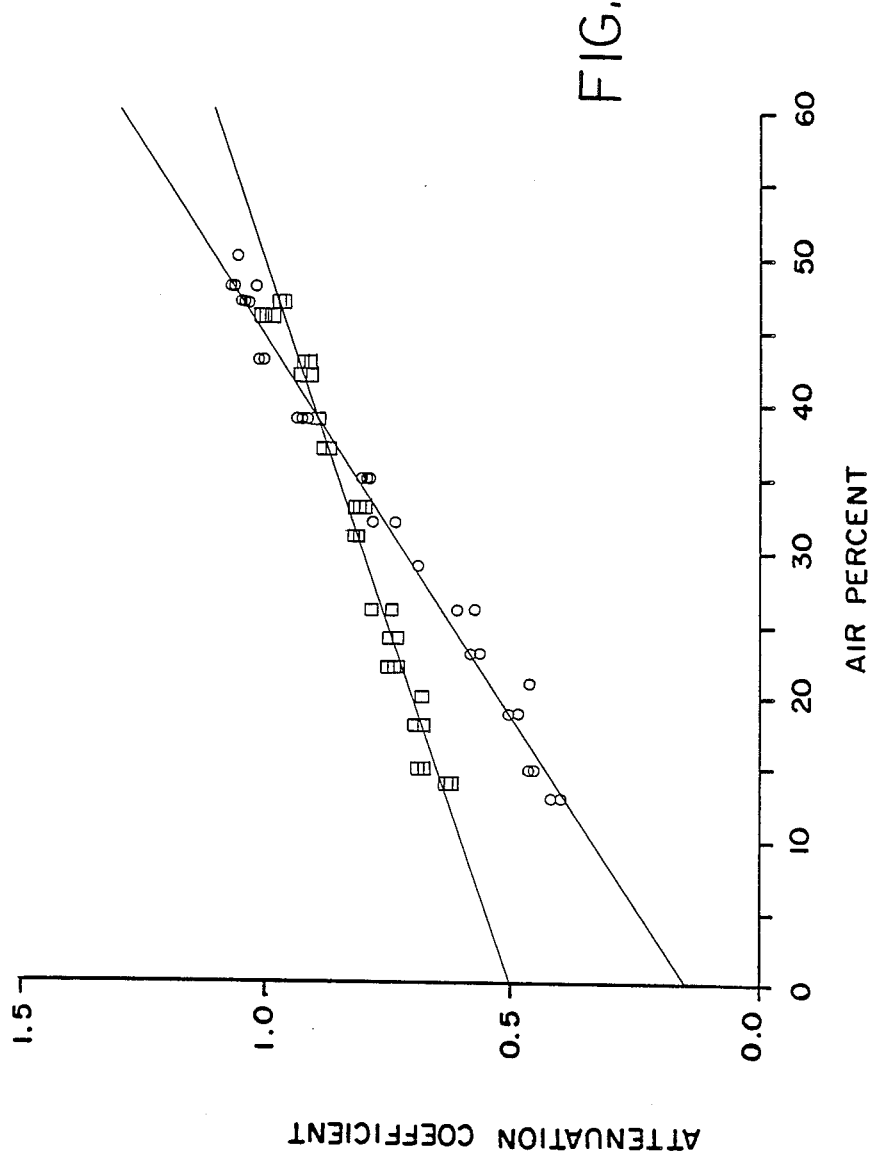

FIGS. 6 and 7 were prepared from measurements made with apparatus of the type shown in FIG. 1a. The vessel was a plexiglas tube. In FIG. 6, the circles plot results for a 2.8 MHz excitation frequency and the squares plot results for a 5.0 MHz excitation frequency. The desired excitation frequency was achieved by selecting a transducer having as its natural ringing frequency the desired excitation frequency. In both cases, the time windows were spaced at 16 and 32 microseconds. The strong linear relationship of air bubble percentage to attenuation coefficient is present.

The results plotted in FIG. 7 are for a more viscous mixture, paraffin oil and air. As expected, the attenuation is higher. The circles plot results measured at 2.0 MHz excitation and the squares indicate 5.0 MHz excitation. The time windows were fixed at 16 and 32 microseconds. Because wave attenuation in paraffin oil is larger at 5 MHz than at 2 MHz, the plotted lines intersect. In FIG. 7, 512 measurements were taken for each plotted point rather than the 1000 measurements per point in FIGS. 4 and 5.

In a particular installation, apparatus according to the invention must be calibrated. The calibration is carried out by introducing a known gas bubble/liquid mixture into the apparatus and making numerous measurements to produce a calibration like the graphs of FIGS. 4-7.

The invention provides superior results to those produced when separate transmitting and receiving transducers are used. In that arrangement, the transmitting and receiving transducers are disposed opposite each other. The launched wave proceeds directly to the receiver and its attenuation is measured. However, in larger vessels where the transducer separation exceeds about 12 cm., the attenuation is so large that reliable measurements cannot be made.

In the embodiment of FIG. 1a, it is important that the acoustic impedance mismatch between the liquid and the vessel wall material not be too large. If the mismatch is too large, very little of the ultrasonic energy will enter the liquid. Instead, the longitudinal wave will primarily echo between the wall surfaces. One solution to an acoustic impedance mismatch is to generate ultrasonic waves that are much shorter, i.e. much fewer wave cycles, than would be used where the transducer contacts the mixture. The first and second time windows are positioned in time so that the wall surface reflections are not detected. The gain of the receiver, e.g. amplifier 205, is increased over the value otherwise used, in order to detect the relatively weak signals attributable to bubble reflection.

In most installations, it is desirable not to measure a fixed bubble concentration, but to monitor gas concentration over a period of time. Repetitive measurements are particularly valuable when the liquid is flowing through the vessel. In these installations, the measurement process described is constantly repeated. The first and second and third time periods occur repetitively and sequentially, so that longitudinal waves are repeatedly launched and two echos are detected over and over. With respect to the embodiment of figures, in the repetitive performance mode, synchronizer 204 generates a train of enabling pulses that first enable pulser 202 and then enable gated voltage detectors 206 and 208, repeatedly and in sequence.

The invention has been described with respect to certain preferred embodiments. Various additions and modifications will occur to those of skill in the art. Accordingly, the scope of the invention is limited solely by the following claims.

I claim:

1. An apparatus for quantitatively measuring the gas bubble content of a liquid containing gas bubbles, said apparatus comprising:
    ultrasonic means for launching, during a first time period, longitudinal waves in a liquid containing gas bubbles;
    a ultrasonic means for detecting, during second and third time periods, longitudinal waves reflected from said gas bubbles and for generating electrical signals in response to detection of longitudinal waves, said first, second and third time periods occurring sequentially without overlap;
    first and second peak signal detectors for sensing the peak amplitudes of electrical signals produced by said second transducer in response to reflected waves detected during said second and third time periods, respectively, and for generating first and second magnitude signals, respectively indicative of the relative peak amplitudes of longitudinal waves detected during said second and third time periods;
    first and second logarithmic amplifiers connected to said first and second peak signal detectors, respectively, for receiving said first and second magnitude signals and for producing first and second logarithmic signals proportional to the logarithms of the amplitudes of said first and second magnitude signals; and
    means receiving said first and second logarithmic signals for comparing said first and second logarithmic signals to each other to determine the gas bubble content in said liquid.

2. The apparatus of claim 1 wherein said means for launching and means for detecting comprise a single ultrasonic transducer.

3. The apparatus of claim 2 wherein said single ultrasonic transducer is affixed to the outside of a wall of a vessel containing said liquid.

4. The apparatus of claim 3 including synchronizing means for activating said single ultrasonic transducer during said first time period and for activating said single ultrasonic transducer during said second and third time periods so that longitudinal waves reflected from said vessel walls are not detected.

5. The apparatus of claim 1 wherein said ultrasonic means far as launching and means for detecting are in contact with said liquid containing gas bubbles.

6. The apparatus of claim 1 comprising electrical signal generating means connected to said means for launching for applying a generated electrical signal to said means for launching during said first time period.

7. The apparatus of claim 1 wherein said means for comparing comprises a differential amplifier receiving said first and second logarithmic signals and generating an output signal proportional to the difference between said logarithmic signals indicating the gas bubble content of said liquid.

8. The apparatus of claim 1 wherein said comparing means includes smoothing means receiving said output signal from said differential amplifier for smoothing the amplitude of said output signal over time.

9. The apparatus of claim 1 including synchronizing means for repetitively and sequentially activating said means for launching during each of a plurality of said first time periods and for repetitively and sequentially activating said means for detecting during each of said consecutive second and third time periods following each said first time period.

10. A method of quantitatively measuring the gas bubble content of a liquid containing gas bubbles, said method comprising:
    launching, during a first time period, longitudinal waves into a liquid containing gas bubbles;
    detecting, during second and third time periods, longitudinal waves reflected from said gas bubbles and generating first and second electrical magnitude signals in response to said waves detected during said second and third time periods, respectively, said first and second magnitude signals having amplitudes indicative of the peak amplitudes of waves detected during said first and second time periods, respectively, said first, second and third time periods occurring sequentially without overlap;
    determining the relative amplitudes of said first and second magnitude signals by generating first and second logarithmic signals proportional to the logarithms of the amplitudes of said first and second magnitude signals, respectively; and
    comparing the relative magnitudes of said first and second logarithmic signals to determine the gas bubble content of said liquid.

11. The method of claim 10 wherein said launching step comprises exciting an ultrasonic transducer with an electrical signal during said first time period to convert said electrical signal to a longitudinal wave.

12. The method of claim 10 including selecting said first second and third time periods to prevent detection of waves reflected from the walls of a vessel containing said liquid.

13. The method of claim 10 wherein said comparing step comprises subtracting said second logarithmic signal from said first logarthmic signal to generate an output signal indicating the gas bubble content of said liquid.

14. The method of claim 13 including smoothing said output signal over time.

15. The method of claim 10 including repetitively and sequentially launching longitudinal waves during each of a plurality of first time periods and detecting reflected waves during each of the said consecutive second and third time periods following each said first time period.

16. The method of claim 15 including determining, after each said third time period and before the next succeeding first time period, the relative magnitudes of said waves detected during the immediately preceding, consecutive second and third time periods.

17. An apparatus for quantitatively the gas bubble content of a liquid containing gas bubbles, said apparatus comprising:

a single ultrasonic transducer affixed to the outside of a wall of a vessel containing a liquid including gas bubbles, said transducer for launching, during a first time period, longitudinal waves in said liquid and for detecting, during second and third time periods, longitudinal waves reflected from said gas bubbles, said first, second and third time periods occurring sequentially without overlap;

synchronizing means for activating said ultrasonic transducer to launch waves during said first time period and for activating said transducer to detect waves during said second and third time periods so that longitudinal waves reflected from said vessel walls are not detected;

means receiving said detected longitudinal waves for determining the relative magnitudes of longitudinal waves detected during said second and third time periods and for generating said first and second magnitude signals indicative of said relative magnitudes; and means receiving said first and second magnitude signals for comparing said first and second magnitude signals to determine the gas bubble content of said liquid.

18. The apparatus of claim 17 wherein said means for determining comprises first and second peak signal detectors for sensing the peak amplitudes of electrical signals produced by said transducer in response to reflected waves detected during said second and third time periods, respectively, and for generating said first and second magnitude signals, respectively, in response to said peak amplitudes.

19. The apparatus of claim 18 wherein said means for determining includes first and second logarithmic amplifiers connected to said first and second peak signal detectors, respectively, for receiving said first and second magnitude signals and for producing first and second logarithmic signals proportional to the logarithms of the amplitudes of said first and second magnitude signals.

20. The apparatus of claim 19 wherein said means for comparing comprises a differential amplifier for receiving said first and second logarithmic signals and for generating an output signal proportional to the difference between said logarithmic signals indicating the gas bubble content of said liquid.

21. A method of of quantitatively measuring the gas bubble content of a liquid containing gas bubbles, said method comprising:

launching from a single ultrasonic through the wall of a vessel and into a liquid including gas bubbles contained within the vessel, during a first time period, longitudinal waves;

detecting with said transducer, during second and third time periods, longitudinal waves reflected from said gas bubbles, said first, second and third time periods occurring sequentially without overlap;

selecting said first, second and third time periods to prevent detection of waves reflected from the walls of a vessel containing said liquid;

determining the relative magnitudes of said longitudinal waves detected during said second and third time periods; and comparing the relative magnitudes of the longitudinal waves detected during said second and third time periods to each other to determine the gas bubble content of said liquid.

22. The method of claim 21 wherein said detecting step includes generating first and second electrical magnitude signals in response to said detected waves during said second and third time periods, respectively, said first and second magnitude signals having amplitudes indicative of the peak amplitudes of said first and second detected waves, respectively, and wherein said determining step includes determining the relative amplitudes of said first and second magnitude signals.

23. The method of claim 22 including generating first and second logarithmic signals proportional to the logarithms of the amplitudes of said first and second magntiude signals, respectively, and wherein said comparing step comprises subtracting said second logarithmic signal from said first logarithmic signal to generate an output signal indicative of the gas bubble content of said liquid.

* * * * *